(12) United States Patent
Garcia da Fonseca

(10) Patent No.: US 8,149,412 B2
(45) Date of Patent: Apr. 3, 2012

(54) DYNAMIC DETECTION DEVICE BASED ON SURFACE PLASMON RESONANCE EFFECT

(75) Inventor: João Garcia da Fonseca, Azambuja (PT)

(73) Assignee: Biosurfit, S.A., Lisbon (PT)

( * ) Notice: Subject to any disclaimer, the term of this patent is extended or adjusted under 35 U.S.C. 154(b) by 368 days.

(21) Appl. No.: 12/514,531

(22) PCT Filed: Nov. 15, 2007

(86) PCT No.: PCT/PT2007/000048
§ 371 (c)(1),
(2), (4) Date: May 12, 2009

(87) PCT Pub. No.: WO2008/060172
PCT Pub. Date: May 22, 2008

(65) Prior Publication Data
US 2010/0039648 A1 Feb. 18, 2010

(30) Foreign Application Priority Data

Nov. 15, 2006 (PT) .......................... 103606

(51) Int. Cl.
*G01N 21/55* (2006.01)
(52) U.S. Cl. ........................................ 356/445; 356/447
(58) Field of Classification Search .................. 356/445, 356/447
See application file for complete search history.

(56) References Cited

U.S. PATENT DOCUMENTS

| 6,570,657 B1 | 5/2003 | Hoppe et al. | |
| 7,407,817 B2 * | 8/2008 | Ho et al. | 436/524 |
| 2003/0030817 A1 | 2/2003 | Lee et al. | |
| 2003/0103208 A1 | 6/2003 | Quinn et al. | |
| 2003/0206290 A1 | 11/2003 | Byrne et al. | |
| 2006/0072113 A1 | 4/2006 | Ran et al. | |
| 2006/0119859 A1 | 6/2006 | Su et al. | |
| 2007/0166763 A1 * | 7/2007 | Ho et al. | 435/7.1 |

FOREIGN PATENT DOCUMENTS

| CH | 19710005260 | 4/1971 |
| WO | 00/46589 A | 8/2000 |

OTHER PUBLICATIONS

Homola, J. et al., "Surface Plasmon Resonance Sensors: Review", Sensors and Actuators 54, pp. 3-15, Elsevier Science S. A., 1999.
Homola, J., "Present and Future of Surface Plasmon Resonance Biosensors", Anal Bioanal Chem, pp. 528-539, Springer-Verlag, 2003.
P. G. de Gennes et al., "The Physics of Liquid Crystals", 2nd Ed. Clarendon Oxford, 608 pages, 1993.
Fonseca, JG, PhD Thesis, Strasbourg, 2001.
G. Vertogen, W, et al., Thermotropic Liquid Crystals: Fundamentals, pp. 25-28 and 125-136.
Hecht, E, "Optics, 4th Edition", Addison Wesley Longman, 704 pages, 1998.

(Continued)

*Primary Examiner* — Roy M Punnoose
(74) *Attorney, Agent, or Firm* — Maier & Maier, PLLC

(57) ABSTRACT

A detection device based on the surface plasmon resonance effect, including a radiation emitter and a radiation detector, a fluidic substrate, a liquid crystal layer and respective control mechanism.

2 Claims, 10 Drawing Sheets

OTHER PUBLICATIONS

Love, Gordon D., Wavefront Control Using a High Quality Nematic Liquid Crystal Spatial Light Modulator, SPIE, vol. 2566, 5 pages, Soc. Foto-Opt. INstrum. Eng. 2566, pp. 43-47, 1995.

H. Ren et al., "Tunable-Focus Flat Liquid Crystal Spherical Lens", Applied Physics Letters, vol. 84, No. 23,, 3 pages, Jun. 7, 2004.

Born, W. et al., Electromagnetic Theory of Propagation, Interference and Diffraction of Light, Pergamon Press, 1989.

Hooper, I. et al., "Differential Ellipsometric Surface Plasmon Resonance Sensors with Liquid Crystal Polarization Modulators", Applied Physics Letters, AIP, American Institute of Physics, Melville, NY, US, vol. 85, No. 15, Oct. 11, 2004, pp. 3017-3019, XP012062845, ISSN: 0003-6951.

Guo, J. et al., "Small-Angle Measurement Based on Surface-Plasmon Resonance and the Use of Magneto-Optical Modulation", Applied Optics, OSA, Optical Society of America, Washington, DC, US, vol. 38, No. 31, Nov. 1, 1999, pp. 6550-6555, XP000893703, ISSN: 0003-6935.

International Search Report dated May 3, 2008 to corresponding PCT/PT2007/000048, 3 pages.

* cited by examiner

Fig. 1ª
(Prior Art)

DYNAMIC DETECTION DEVICE BASED ON SURFACE PLASMON RESONANCE EFFECT

RELATED APPLICATIONS

This application claims priority, under 35 U.S.C. §119, to International Patent Application No.: PCT/PT2007/000048, filed on Nov. 15, 2007, which claims priority to Portuguese patent application No.: PT 103606, filed Nov. 15, 2006, the disclosures of which are incorporated by reference herein in their entireties.

TECHNICAL FIELD

The present invention relates to electro-optic sensors based on the Surface Plasmon Resonance (SPR) effect, in particular to processes and devices used for the detection of chemical and/or biological events comprising the following elements: (1) a radiation emitter (20) and a radiation detector (30); (2) a Detection Zone (DZ) (41) containing a Detection Surface (DS) (42) which incorporates a thin conductive layer built to allow for the occurrence of the SPR effect, for at least one angle of incidence and at least one wavelength of the radiation incident onto the DS (42); (3) a fluidic substrate (40) including channels (43) and at least one DZ described in (2); (4) a fluid control mechanism used to deliver a predefined fluid volume from an initial reservoir into a DZ and from there to a final reservoir; (5) a liquid crystal layer (LCL) (80), placed between the radiation emitter (20) and the radiation detector (30), controlled by electrical, magnetic or optical means, and used in such way that enables the control of the radiation properties and leading to an optimized SPR signal, improving in this way the accuracy and sensitivity of the detection device.

Chemical/Biological Detection Devices

A Chemical/biological detection device is composed by three major elements: (A) Recognition elements, capable of recognizing a specific chemical and/or biological substance; (B) Transduction mechanisms, capable of converting the chemical/biological recognition events into quantitative information; (C) Fluidic mechanisms, capable of delivering fluid samples to the recognition elements in a controlled manner.

(A) Recognition Element

Recognition elements are typically based on the key-lock principle, and comprise molecular regions or combinations of the same capable of recognizing specific chemicals or biological substances, from now on referred to analyte. There are different ways to achieve this effect, namely: randomly or oriented enzymes, lectines or antibodies. The performance of this recognition element is dependent on several parameters, namely: (i) the sensitivity (defined by the detection limit); (ii) the specificity (defined by the degree of sensitivity for detecting other substances present in the same medium of the specific analyte to be detected); (iii) its stability over time. In the case of chemical/biological detection devices used for determinations involving proteins or enzymes, the recognition elements usually consist of immobilized layers containing specific and oriented antibodies.

The chemical/biological recognition element may be obtained using several different mechanisms, namely: (i) chemical adsorption to the surface; (ii) encapsulation on a polymeric matrix; (iii) covalent bonding to a solid substrate. Although the choice of the chemical/biological recognition element is beyond the scope of the present invention, the description presented above serves only has a framework overview of the most common possibilities for building this biosensing element.

(B) Transduction Mechanism

There are several transduction mechanisms capable of converting chemical/biological events into quantitative information for subsequent treatment and analysis, namely electrochemical, vibratory, magnetic and optic transducers.

The optical detection of the SPR effect is essentially a measurement technique of the refractive index close to an electrically conductive surface. The most significant difference of SPR detection compared to conventional refractometers relates to the measurement scale and detection process: in conventional techniques, all the fluid volume contributes to the optical response which results in a average measure of the refractive index; On the contrary, in the case of SPR detection, only the volume of the fluid close to a conducting surface is relevant. Moreover, in this later case, the measure corresponds to a weighted average of the refractive index with a decaying weight when moving apart from the conductive layer in which the SPR effect occurs.

SPR Effect

The SPR effect is an optical phenomenon that results from the local charge density oscillation in an interface between two media of differing dielectric properties. In particular, the SPR effect occurs at the interface between a dielectric medium and a metallic one (see reference 1). In this case, the surface plasmon wave is an electromagnetic wave with polarization TM (magnetic vector of the wave is perpendicular to the propagation direction and parallel to the interfacial plan). The SPR propagation constant $\beta$ may be described by equation (1):

$$\beta = \lambda \sqrt{\frac{\varepsilon_m \varepsilon_d}{\varepsilon_m + \varepsilon_d}} \qquad (1)$$

in which $\lambda$ is the incident wavelength, $\varepsilon_m$ is the dielectric constant of the metal ($\varepsilon_m = \varepsilon_{mr} + i\varepsilon_{mi}$) and $\varepsilon_d$ is the dielectric constant of the dielectric medium. The SPR only occurs if $\varepsilon_{mr} < 0$ and $|\varepsilon_m| < \varepsilon_d$. In this case, the SPR effect will propagate at the interface between the two media and will decrease exponentially from the interface to the bulk of each medium. On the other hand, the SPR effect is only detectable for metallic films with thicknesses in the range of tens to hundreds of nanometer (in the case of a gold film, the SPR effect typically occurs with thicknesses between 25 nm and 150 nm).

Due to these facts and according to equation (1), the propagation constant $\beta$ of the SPR is extremely sensitive to variations of the refractive index in the dielectric medium close to the interface. As a consequence, the SPR effect may be exploited for sensing applications, e.g. the immobilization of a certain biological material (protein, enzyme, etc.) close to the interface will result in a local variation (at the nanometer length scale) of the refractive index (since typically the refractive index of water-based solutions is around 1.33 and the refractive index of biological compounds is close to 1.54). This change on the refractive index induces a change on the propagation constant of the surface plasmon that may be detected with precision by optical means, as described in the following sections.

SPR Configurations

There are three basic methods for detecting the SPR effect:
(i) Measuring the intensity of radiation reflected from the detection surface as a function of the radiation incidence angle; typically, for a given wavelength, the SPR effect is clearly detected at a specific incidence angle in which the reflection is minimal;

(ii) Measuring the intensity of radiation reflected from the detection surface as a function of the radiation wavelength; typically, for a fixed incidence angle, the SPR effect is clearly detected at a specific radiation wavelength in which the reflection is minimal;

(iii) Measuring the phase of radiation reflected from the detection surface as a function of the incidence angle or radiation wavelength. In this case, the SPR effect is clearly detected at a specific incidence angle or radiation wavelength in which the radiation phase variation is maximal.

Different optical configurations may be used in order to properly detect the SPR effect (see reference 2), using typically an optical system that both creates surface plasmon (using an illumination element, e.g. a laser or a radiation emitting diode or any other appropriate radiation source) and also detects the SPR effect (using an optical measurement element, e.g. CCD, CMOS, photodiode, or any other appropriate element).

The SPR effect only occurs if the component of the vector of incident wave that is parallel to the interfacial plane is coincident with the component of surface plasmon wave. This specific condition will only exist if there is some coupling mechanism typically provided by (i) a prism; (ii) a waveguide; (iii) a diffraction grating. The man of the art may rapidly understand these coupling techniques by reading technical literature, namely by reading reference 1.

(C) Fluidic Mechanism

Different mechanisms may be used for the fluid control, namely conventional fluid pumping using external pumps and tubes, electro pressure control, acoustic/piezoelectric control, electrokinetics, and centrifugal control. The optimization of this element of chemical/biological detection device is beyond the scope of the present invention.

Liquid Crystal Layers

Liquid crystal (LC) phases, or mesophases, are intermediate phases between liquids and crystals, presenting orientation properties (see reference 3). A specific type of LC, named nematic LC, presents an order on the orientation of its molecules combined with a disorder on the position of its molecules. It is possible to define an average orientation direction of the LC molecules that propagates through long distances, with this direction defined, for example, by a certain alignment surface. Moreover, for certain LC molecules, it is possible to use an external electric field that also induces a specific orientation. In this case, the orientation of the LC molecules depends on the competition between the anchoring surface properties (induced by the alignment surface) and the coupling electric field forces (see reference 4).

The LC layers present two relevant properties:
(1) an optical anisotropy resulting in a mismatch on the radiation propagation through the LC layer, in terms of the radiation polarization parallel or perpendicular to the average orientation of the LC molecules;
(2) a gradual change of the average orientation of the LC molecules along an LC layer induces changes on the polarization properties of the radiation passing through the LC layer. In particular, if the LC molecules present a twisting pitch along the LC layer that is much larger than the radiation wavelength, then the system will behave like a waveguide (in which the radiation polarization follows the rotation of the LC molecules). This is the basic principle of the standard LC devices according to the invention of M. Schadt (see reference 5). Now, if the twisting pitch of the LC layer is of the same order as the radiation wavelength, then smaller rotations of the radiation polarization will occur, and/or reflections and/or inverse radiation polarization rotations, depending on the wavelength/pitch ratio.

There are different types of LC layers with potential use for optical systems. The most common type of LC layer, called twisted nematic LC, is based on the continuous twisted orientation of the average direction of the LC molecules along the LC layer. The LC layer is characterized in that a twisting pitch depends on several parameters, namely the concentration of a chiral dopant that induces the twisting. When subject to an external electric field, the LC molecules tend to be aligned along the field and the twisting is then destroyed. By controlling the applied electric field it is possible to properly adjust the LC layer twisting pitch. For systems in which there is a need to maintain the optical quality (e.g., without radiation diffusion) some types of LC layers are no longer suitable (namely, PDLC layers, or other LC layers with significant radiation diffusion).

Conventional SPR Detection Devices

Conventional SPR detection devices include an optical system with pre-defined and fixed properties, namely in terms of incidence angles, polarization and wavelength.

FIG. 1A is a schematic illustration of a conventional SPR detection device according to the prior art, in the prismatic configuration. A radiation emitter (20) produces a radiation beam (101) focused through a prism (90) into a detection surface DS (42) situated in a detection zone DZ (41). The DS includes a thin conductive layer in close proximity with the fluid. The radiation reflected (102) is directed to the radiation detector (30). The analysis of the radiation signal observed in the radiation detector (30) is used for the quantitative measurement of the concentration of substances or of chemical and/or biological events occurring in the vicinity of the DS (42). In this configuration, the device presents fixed and pre-defined optical properties, namely in terms of radiation wavelengths, phase and incidence angles.

FIG. 1B is a schematic illustration of a conventional SPR detection device according to the prior art, in the grating coupling configuration. A radiation emitter (20) produces a radiation beam (101) focused through a prism (90), into a detection surface DS (42) situated in a Detection Zone DZ (41). The DS includes a thin conductive layer behaving like a diffraction grating. The radiation reflected (102) is directed to the radiation detector (30). The analysis of the radiation signal observed in the radiation detector (30) is used for the quantitative measurement of the concentration of substances or of chemical and/or biological events occurring in the close proximity of the DS (42). Again, in this configuration, the device presents fixed and predefined optical properties, namely in terms of radiation wavelengths, phase and incidence angles.

In this configuration, the radiation emitter (20) has fixed and pre-defined optical properties, namely in terms of:
  the wavelength spectra, this parameter may be pre-defined by using a laser for the radiation emitter (20), or by using a radiation emitter (20) with a continuous emission spectra, such as a LED or any other source of continuous spectra;
  the range of incident angles of the radiation incident on the DS (42), defined by the optical elements used, namely by the optical lenses setup the radiation emitter (20);
  the polarization of the incident radiation, typically fixed linear or circular, when using lasers in the radiation emitter (20), or non-polarized radiation when using LEDs;

the phase of the incident radiation. If a laser is used for the radiation emitter, typically the radiation is coherent in the radiation cone incident on the DS (42);

the focal point of the radiation incident on the DS (42);

the refractive index of the material used as substrate in contact with the DS (42);

the refractive index of the standard fluid used to perform the SPR measurements.

These different parameters are pre-defined and fixed in conventional SPR detection devices, and this fact presents a limitation on their potential use. In particular, it is a limiting factor in terms of detection range of the fluid refractive index in contact with the DS (42). Moreover, the limitations, associated with detection noise and angular resolution of the radiation detector (30) sensor (i.e. the relation between angular aperture of the incident radiation and number of detection elements in the sensor), are also a limiting factor of the resolution and sensitivity of conventional SPR detection devices.

These facts limit both the sensitivity and the application range of SPR detection. In particular, conventional SPR detection devices present the following limitations:

(1) difficulty in eliminating optical defects (mechanical fatigue, radiation diffusion, refractive index changes), resulting in a noise signal higher than desired. This fact is particularly relevant when detecting small biological substances;

(2); difficulty in distinguishing the SPR sensor signal due to receptor-analyte binding and refractive index changes of either the fluid or the DS (42) substrate due to temperature changes. This fact limits the extrapolation of SPR measurements into quantitative information regarding analyte concentration present near the DS (42) (see reference 6);

(3) difficulty in adjusting the detection parameters for maximum sensitivity at the DS (42) for the desired thickness corresponding to the size of the analyte;

In order to overcome these limitations, the present invention considers the use of a LC layer (80) placed between the radiation emitter (20) and the radiation detector (30), controlled by electric, magnetic or optical means, in order to adjust the radiation properties and in this way amplify the SPR signal observed at the radiation detector (30).

The patent US2003103208 refers to a SPR sensor with a prismatic configuration, using an LC layer placed between the radiation emitter and a conductive layer defining the DS, in order to rotate the radiation polarization by 90°. In this case, the radiation incident on the DS may have two polarization states: (i) TM polarization (parallel to the interface) or (ii) TE polarization (perpendicular to the interface). The patent mentioned above only applies to SPR sensors in the prismatic configuration and to devices wherein the radiation polarization is rotated by 90°.

The patent EP1157266 refers to an SPR detection device, mentioning that it would be possible to use a LC layer behaving like a controllable polarizer. The referred patent applies to SPR sensor devices based on diffractive reflective optical elements. Moreover, in the above-mentioned patent there is no mention on the possible embodiment of the referred LC layer.

Patents EP1068511 and US2003206290 concern an SPR detection device in which LC layers are used as controllable diaphragms by electric means, in order to select the time period and placement of the radiation beam necessary for the SPR effect.

The following publications are included here for reference:
1. Homola, J. Et al. Sensors and Actuators 54, 3-15 (1999);
2. Homola, J. Anal Bioanal Chem 377, 528-539 (2003);
3. P. G. de Gennes, J. Prost, The Physics of Liquid Crystals (2nd ed. Clarendon, Oxford 1993)
4. Fonseca, J G, PhD Thesis, Strasbourg 2001
5. Helfrich, W., Schadt, M. patent CH19710005260
6. G. Vertogen, W. H. de Jeu: *Thermotropic Liquid Crystals: Fundamentals* (EPSinger-Verlag, Berlin, 1988)
7. Hecht, E. Optics, Addison Wesley Longman (1998).
8. Gordon D. Love. Proc. Soc. Foto.-Opt. Instrum. Eng. 2566: 43-47 (1995).
9. H. Ren et al, Appl. Phys. Lett. 84, 4789 (2004).
10. Born, M. and Wolf, E. Principles of Optics: Electromagnetic Theory of Propagation, Interference, and Diffraction of Light, Pergamon Press (1989).

OBJECT OF THE PRESENT INVENTION

We have come to the conclusion that it would be relevant to dynamically adjust some parameters significant for the SPR effect, in order to optimize the respective SPR detection device performance. In this frame, LC layers are found to be appropriate and advantageous, since it is possible to adjust the radiation properties (reflected radiation or transmitted radiation) by controlling a LC layer using simple electric or optic means. This adjustment of the radiation properties, when coupled to a detection device based on the SPR effect, may be explored in order to enhance its overall performance.

In a first aspect, the present invention comprises an optical system consisting of a radiation emitter (20) and a radiation detector (30) both used for detecting events occurring in the close proximity of a DS (42), which includes a thin electrically conductive layer in a fluidic substrate, containing channels (43) and at least a DZ (42). The DZ (42) is built in such a way that it enables the occurrence of the SPR effect, which is used for the detection of chemical and/or biological events. The detection device also includes a LC layer (80) placed in between the radiation emitter (20) and the radiation detector (30), controlled by electrical or optical means. The LC layer (80) is controlled in such a way that enables the controlled adjustment of the radiation properties in order to optimize the accuracy and sensitivity of the detection device.

In a second aspect, the present invention consists of a SPR sensor (10) capable of detecting chemical and/or biological events in the close proximity of a DS (42), comprising a fluidic substrate (40) and an optical system, wherein the optical system comprises a radiation emitter (20) and a radiation detector (30) and a LC layer (80) placed in the radiation path between the radiation emitter (20) and the radiation detector which is capable of adjusting the radiation properties. The SPR sensor (10) is capable of detecting:

(i) the presence of a specific substance, and/or
(ii) the occurrence of a specific chemical and/or biological event in one of the detection zones of the fluidic substrate, The arrangement of the radiation emitter (20) and radiation detector (30) with respect to the fluidic substrate (40) is fixed in such a way that the radiation beam incident on the DS (42) contains at least one incident angle for which there is a coupling on the thin electrically conductive layer resulting in the SPR effect. This configuration is influenced by several properties and parameters, in particular:

The wavelength of the radiation incident on the DS (42);
The refractive index, extinction coefficient and thickness of the electrically conductive layer;
The incidence angle;
The radiation polarization;
The refractive index and extinction coefficient of the fluid present at the DZ (41).

In this sense, and having all parameters fixed, it is possible to observe a change in the radiation pattern of the SPR sensor (10) and from this information to quantify the change on the refractive index in the close proximity of the DS (42). This determination is then used in order to quantify the surface immobilization of a certain substance or the reaction of two types of molecules in the proximity of the DS (42).

The embodiments of the present invention enable proper adjustment of the different parameters mentioned above, in a dynamic way and during the detection process, by using an additional LC layer (80), also placed in the radiation path between the radiation emitter (20) and the radiation detector (30). The different embodiments described in the following sections correspond to different solutions for existing problems of conventional SPR detection devices.

BRIEF DESCRIPTION OF THE DRAWINGS

FIG. 1A is a schematic illustration of a conventional SPR detection device according to the prior art, in the prismatic configuration.

DETAILED DESCRIPTION OF THE INVENTION

Figure 1B:
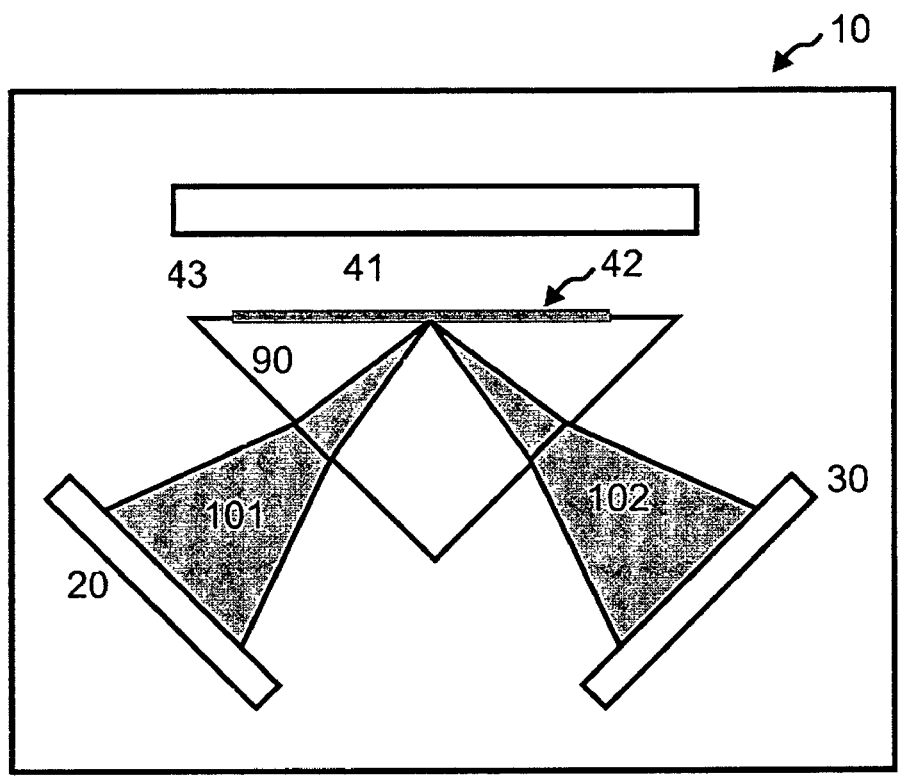
FIG. 1B is a schematic illustration of a conventional SPR detection device according to the prior art, in the grating coupling configuration.
Figure 1B:
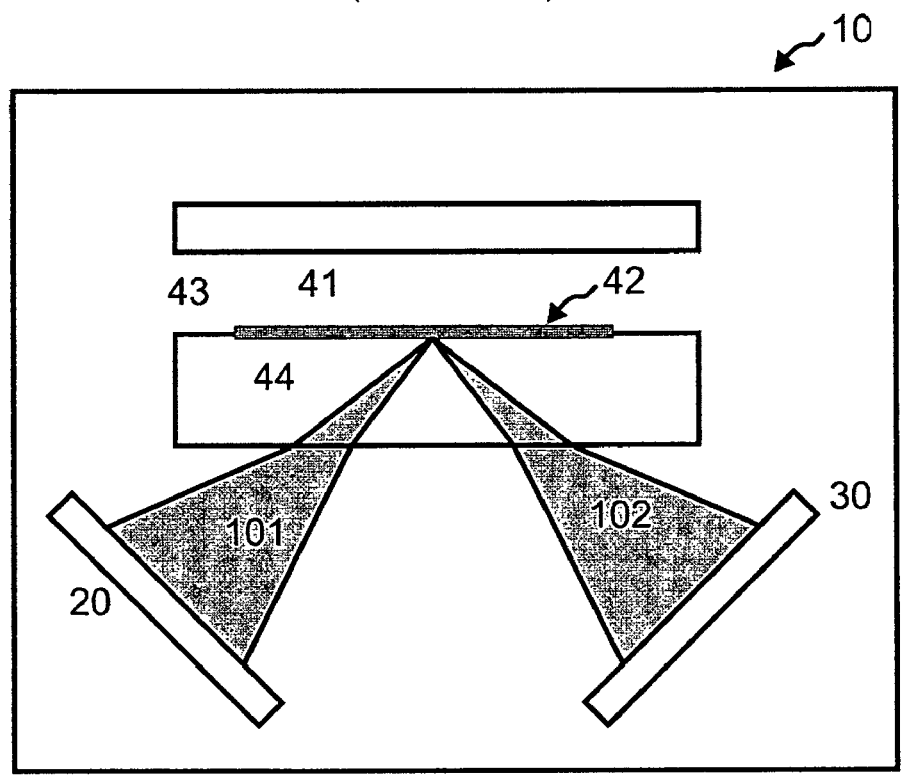

In a first aspect, the present invention consists of an SPR sensor (10) used for detecting chemical and/or biological events, comprising a radiation emitter (20) and a radiation detector (30) used for detecting events occurring in the close proximity of a DS (42) of a DZ (41) of a fluidic substrate (40), comprising channels (43), and at least one DZ (41). The DZ (41) contains a DS (42), which includes a thin electrically conductive layer, built in such a way that enables the occurrence of the SPR effect. The SPR sensor (10) includes a LC layer (80), positioned in the radiation path between the radiation emitter (20) and the radiation detector (30), and controlled by electrical or optical means, enabling the proper adjustment of the radiation properties, to optimise the SPR optical signal. The proper adjustment of the radiation properties using the LC layer (80) leads to enhanced sensitivity and accuracy of the SPR detection device.

In a second aspect, the present invention consists of a SPR sensor (10) capable of detecting chemical and/or biological events occurring in the close proximity of a DS (42), comprising a fluidic substrate (40) and an optical system, wherein the optical system comprises a radiation emitter (20) and a radiation detector (30) and an LC layer positioned between the radiation emitter (20) and the radiation detector (30). The LC layer (80) is capable of adjusting the radiation properties.

The SPR sensor (10) is capable of detecting:
(i) the presence of a specific substance, and/or
(ii) the occurrence of a specific chemical and/or biological event in one of the detection zones.

The embodiments of the present invention enable proper adjustment of the different parameters mentioned above, in a dynamic way and during the detection process, by using an additional LC layer (80), positioned in the radiation path between the radiation emitter (20) and the radiation detector (30). The different embodiments described in the following correspond to different solutions for existing problems of conventional SPR detection devices.

FIRST EXAMPLE

The SPR effect occurs in the component of the radiation polarization that is parallel to the interface (TM polarization) between a thin electrically conductive layer and a dielectric layer. Conventional SPR sensors typically maximize the intensity of the incident radiation in this polarization in order to maximize the SPR signal. The absence of a reference signal is considered problematic for the detection. In particular, the lack of reference signal results in a high (higher than desired) signal noise, due to different sources, namely the lack of stability and uniformity of the radiation source and of the substrate used for the detection. One simple way to eliminate this problem consists in rotating, in a controlled and systematic way, the polarization of the incident radiation. Since the noise is, in a first analysis, independent of the radiation polarization, one may then eliminate a significant part of the acquisition noise by acquiring two signals of different polarizations. For example, by acquiring two signals with TE and TM polarizations and dividing (TM/TE) or subtracting (TM−TE) the two signals it is possible to isolate only the contribution of the SPR effect. This process may the performed using a LC layer (80) with well-known properties.

Figure 2A:
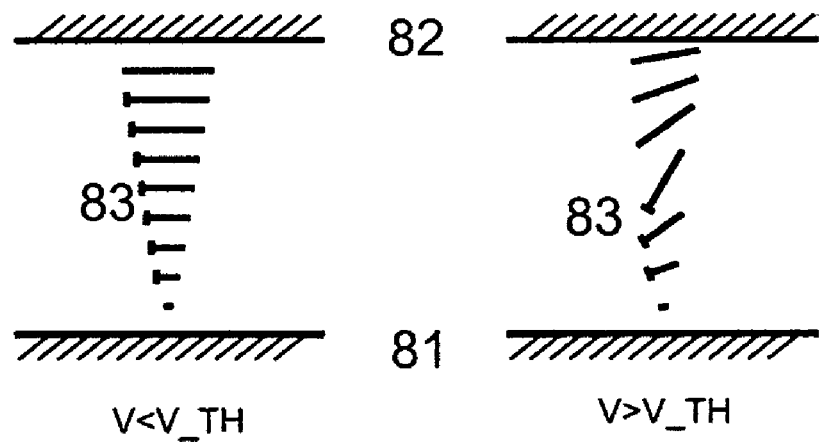
FIG. 2A is a schematic illustration of the average orientation of the molecules in a twisted nematic LC layer. In the rest condition the molecules present a rotation of 90° along the LC layer (left) and when subject to an external electric field above a certain threshold (V_th) the twist is minimized and the molecules became aligned along the electric field (right).

FIG. 2A is a schematic illustration of the average orientation of the molecules in a twisted nematic LC layer. In the rest condition (V<Vth) the average orientation of the LC molecules (83) present a rotation of 90° along the LC layer (left). For sufficiently high applied voltages (V>Vth) the LC molecules (83) tend to be aligned along the electric field and the twist is gradually minimized.

Figure 2B:
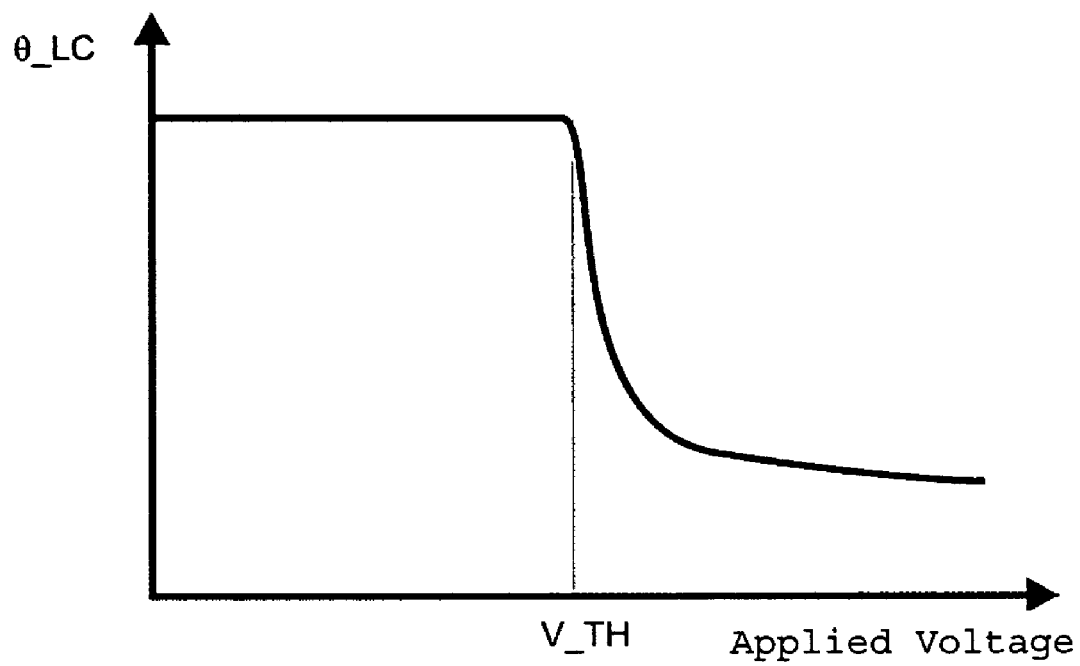
FIG. 2B is a schematic illustration of the behaviour of the total twisting angle of the LC layer illustrated in FIG. 2A as a function of the applied voltage, for high enough voltages the twisting angle tends to zero.

FIG. 2B is a schematic illustration of the behaviour of the total twisting angle of the LC layer described in FIG. 2A, as a function of the applied voltage. If the twisting pitch is sufficiently large when compared with the electromagnetic radiation wavelength, then the LC layer (80) behaves like a wave-guide, so that the incident radiation polarization is rotated along the LC rotation.

Using, for example, a LC layer (80) with a twisting pitch of eight times its thickness, the LC layer (80) will then show two typical states depending on the applied voltage:
(i) when the applied voltage is sufficiently low (e.g., for a planar orientation, the applied voltage is below the Frederiks threshold, see reference 3) then the LC layer (80) induces a rotation of 90° of the incident radiation polarization. The incident radiation may then be selected and aligned in order to have a 90° rotation of its polarization when passing through the LC layer (80) and then be incident on the DS (42) with the TM or TE polarizations while maintaining its relative intensity;
(ii) when subjected to a sufficiently high voltage, the rotation of the LC molecules (83) is destroyed as they tend to be aligned with the applied electric field. In this case, the radiation incident on the DS (42) will only have one polarization component (e.g. TM).

The novelty of the present invention consists of a device comprising:
(i) a fluidic substrate (40) including at least one DZ (41) with a DS (42) built in such a way that it enables the occurrence of the SPR effect;
(ii) a group of radiation emitter (20) and radiation detector (30) arranged in such a way that the radiation incident onto the DS (42) includes a range of angles in which the SPR effect occurs;
(iii) a LC layer (80) positioned in the radiation path between the radiation emitter (20) and the radiation detector (30) built in such a way that it behaves like a wave-guide, so that the polarization of radiation passing through the LC layer (80) is also rotated, enabling the SPR sensor 10 to accomplish the following sequence of events.
(1) Reference Tension Control. The LC controller (84) applies a sufficiently low voltage on the LC layer (80) so that the LC molecules (83) impose a rotation of the polarization of radiation incident on the DS (42).
(2) Reference Signal Acquisition. The first signal S1 is acquired by the radiation detector (30) corresponding to a condition in which the two polarization components (TE and TM) are present in the radiation incident on the DS (42). The acquisition of the signal S1 must occur after a certain time from the applied reference tension (typically in the order of ms) in order to have all the LC molecules out of the transitory orientation regime.
(3) Tension Measurement Control. The LC controller (84) applies a sufficiently high voltage on the LC layer (80) so the LC molecules (83) are aligned with the applied electric field destroying the natural twisting. Due to this alignment, there is no rotation of the polarization of radiation incident on the DS (42).
(4) Signal Measurement Acquisition. The second signal S2 is acquired by the radiation detector (30) that corresponds to a condition in which only one polarization component (e.g. TM) is present in the radiation incident on the DS (42). The acquisition of the signal S2 must occur after a certain time from the applied reference tension (typically in the order of ms) in order to have all the LC molecules out of the transitory orientation regime.
(5) Signal Processing. Finally the SPR signal is extracted from the two optical signals using the relation:

$$S_{SPR} = \frac{S_2}{2S_1 - S_2} \quad (2)$$

Figure 3A:
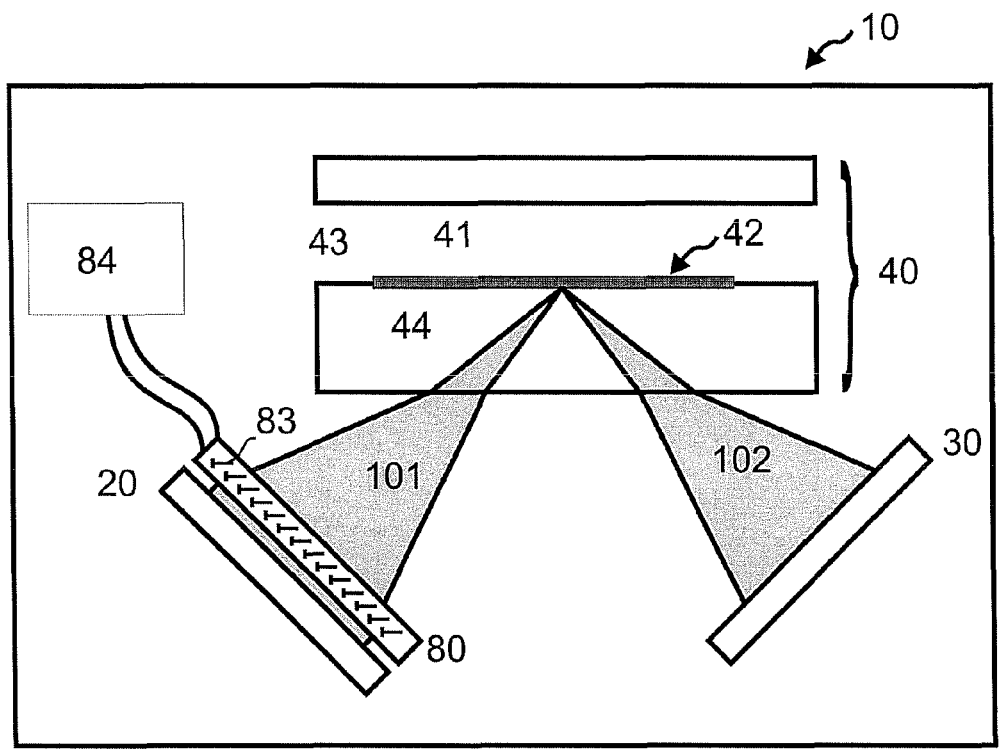
FIG. 3A is a schematic illustration of a SPR detection device in the grating coupling configuration and using a LC layer to control the polarization of the radiation incident in the detection surface.

FIG. 3A is a schematic illustration of a SPR detection device (10) in the grating coupling configuration and using a LC layer (80) to control the polarization of the radiation incident in the DS (42). The radiation emitter (20) irradiates a light beam (101) incident on the LC layer (80) that presents in its initial state a total twist of 45° of the average orientation of the LC molecules (83). The LC layer (80) presents a large twisting pitch when compared to the radiation wavelength behaving like a wave-guide. The LC layer (80) is connected to controller (84) able to apply electric tensions and in this way fine-tune the total twist of the incident radiation polarization (101) on the DS (42). Analyzing the signals detected on the radiation detector (30) corresponding to the different applied voltages, enables the determination of real-time reference signals, eliminating in this way a significant part of the SPR signal acquisition noise. After passing the LC layer (80), the radiation beam is transmitted over a transparent substrate (44) and is incident on the DS (42) that includes a thin electrically conductive layer behaving like a diffraction grating. The DS (42) is in direct contact with a fluid. The reflected signal (102) is then incident on the radiation detector (30). From the analysis of the optical signals on the radiation detector (30) it is possible to quantitatively determine the concentration of the analyte in the close proximity of the DS (42).

Figure 3B:
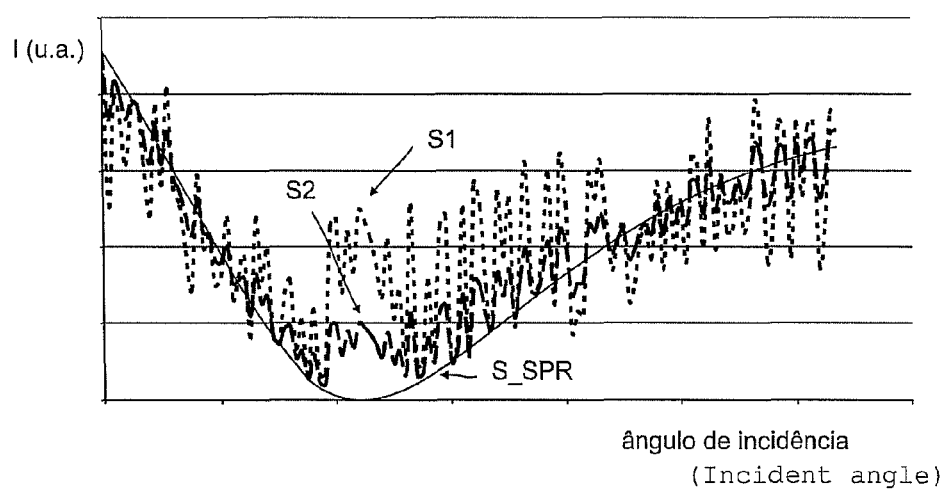
FIG. 3B is a schematic illustration of the embodiment of the device described in FIG. 3A, after acquiring two signals (S1 and S2) with different polarizations being possible to minimize the acquisition noise by dividing the two signals and obtain a final signal (S_SPR) with optimized signal to noise ratio.

FIG. 3B is a schematic illustration of the embodiment of the device described in FIG. 3A. An initial signal S1, corresponding to a linear polarization of the incident radiation (101) at 45° (with respect to the TM polarization direction) contains a significant optical noise that prevents a precise measurement. By applying the proper electric voltages to the LC layer (80) it is possible to obtain a second optical signal S2, corresponding to the TM polarization of the incident radiation (101) (0°). This second signal still contains a significant noise level. By properly dividing both signals one determines the SPR signal and eliminates almost all the noise, since this noise is mostly polarization-independent.

One should note that this concretization only enables the proper measurement of the SPR effect if the delay between the two signals S1 and S2 is small compared to the dynamics of the acquisition noise, since this approach is only valuable for polarization-independent noise.

The radiation incident (101) on the LC layer (80) should preferably be collimated in order to have a uniform and constant rotation of the radiation polarization. In this case, the optical elements used for focusing the radiation incident on the DS (42) should be placed between the LC layer (80) and the fluidic substrate (40) that contains the DS (42). Alternatively, the man of the art may place the LC layer (80) in a region in which the radiation is not collimated, as long as the dependency of the polarization rotation as a function of the incident angle is taken into account. This example may easily be extended to other similar situations wherein the rotation of the LC layer is smaller or higher than 45°, or if the polarization of the incident radiation is different. As a general rule, the SPR signal S_SPR is obtained from the relation:

$$S_{SPR} = \frac{a_1 S_2}{b_1 S_1 - c_1 S_2} \quad (3)$$

in which a1, b1 and c1 are parameters that depend on the initial rotation angle of the LC molecules (83), on the total initial twist of the LC layer (80), its thickness and the applied electric voltages.

Other methods for controlling the LC layer (80) may be considered, as long as it is still possible to control the degree of rotation of the LC molecules (83). For example, is it possible to use a magnetic actuator, and in this case one must consider that typically LC molecules tend to align perpendicularly to the direction of the applied magnetic field. One may also consider a variation of the present embodiment, in which the LC controller (84) keeps the electric voltage amplitude constant and only the electric signal frequency is varied. In this case the man of the art must select the proper frequency range in which the LC molecules response is strongly dependent of the applied electric signal frequency.

SECOND EXAMPLE

Conventional SPR detection devices based on the detection of reflected radiation intensity are based on the measurement of radiation intensity levels of the reflected radiation as a function of the incidence angle. In this case, the SPR effect is clearly identified by a strong decrease of the reflected radiation intensity for a specific incidence angle. So the SPR detection is based on the determination of the temporal evolution of the reflected radiation minimum. In an alternative approach, it is possible to measure the variation of the relative phase of the reflected radiation, since this latter shows a much sharper transition in the SPR effect than the transition observed in radiation intensity, as illustrated on FIG. 4A.

Figure 4A:
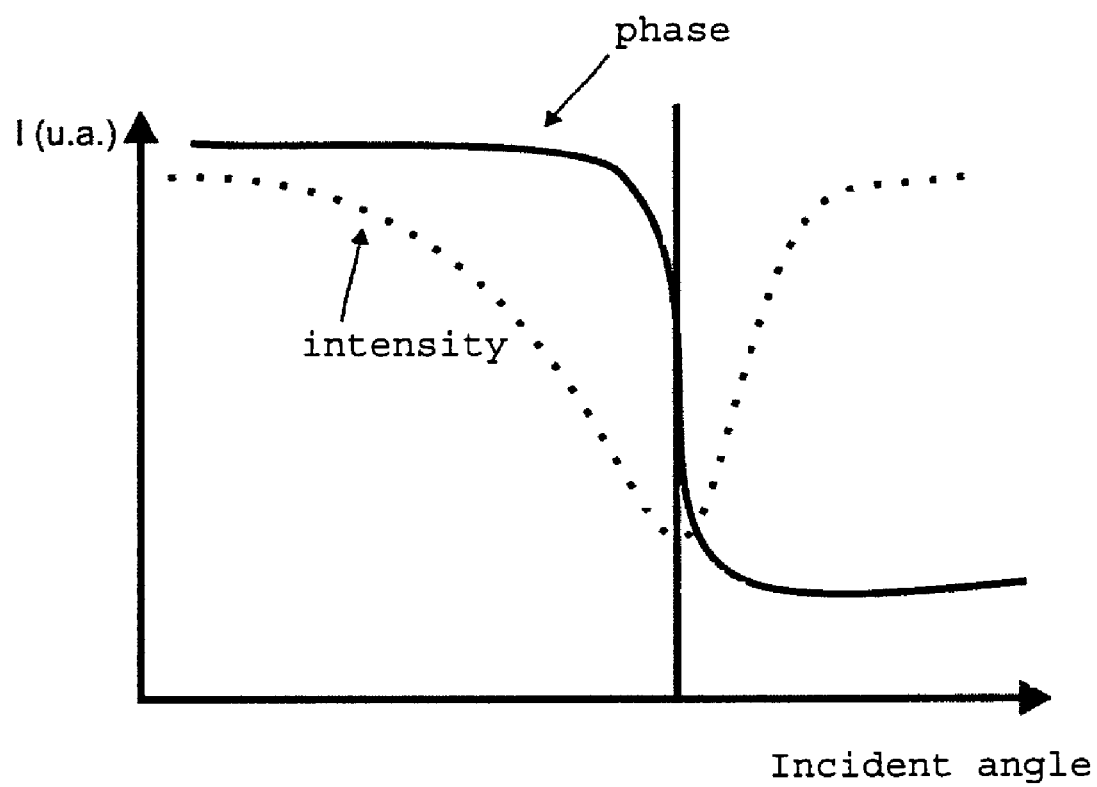
FIG. 4A is a schematic illustration of the behaviour of SPR effect in terms of radiation intensity (dashed line) and radiation relative phase (solid line) both as a function of the incidence angle on the detection surface.

FIG. 4A is a schematic illustration of the behaviour of SPR effect in terms of radiation intensity (dashed line) and radiation relative phase (solid line) both as a function of the incident angle on the DS (42). The relative phase shows a much sharper transition at the SPR coupling than the radiation intensity. This fact may be explored in order to build SPR detection devices with better resolution.

Although there are intrinsic advantages in the phase-measurement configuration, its implementation in conventional SPR detection devices is particularly difficult. On the other hand, it is possible to use a LC layer (80), built in such a way that it enables the proper adjustment of the radiation de-phasing, according to FIGS. 4B and 4C.

Figure 4B:
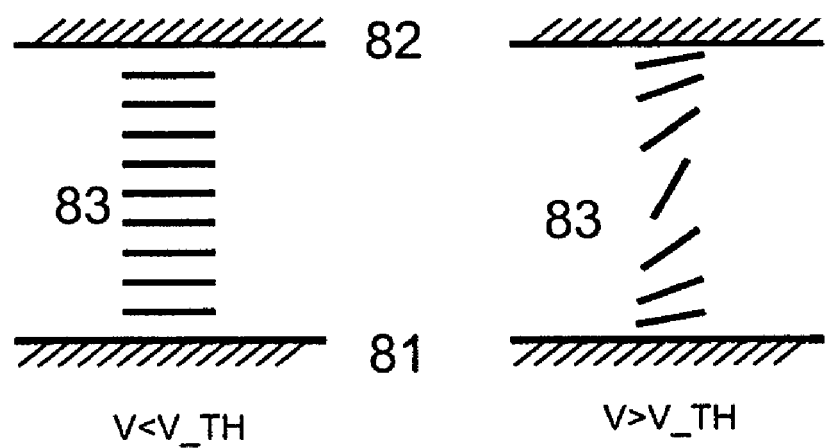
FIG. 4B is a schematic illustration of the average orientation of the molecules in a uniform nematic LC layer. In the rest condition, the molecules average orientation is uniform and aligned along the alignment surface direction (left), and when subject to an externally applied electric field above a certain threshold (V_th) the molecules become aligned with the electric field.

FIG. 4B is a schematic illustration of the average orientation of the LC molecules (83) in a uniform nematic LC layer (80). Due to the anisotropic nature of the LC molecules a de-phasing between the TE and TM polarization components of the radiation is observed. In the rest condition (V<Vth) the molecules average orientation is uniform and parallel to the surface, and when subject to sufficiently high external electric fields (V>Vth) the LC molecules (83) tend to be aligned along the electric field.

Figure 4C:
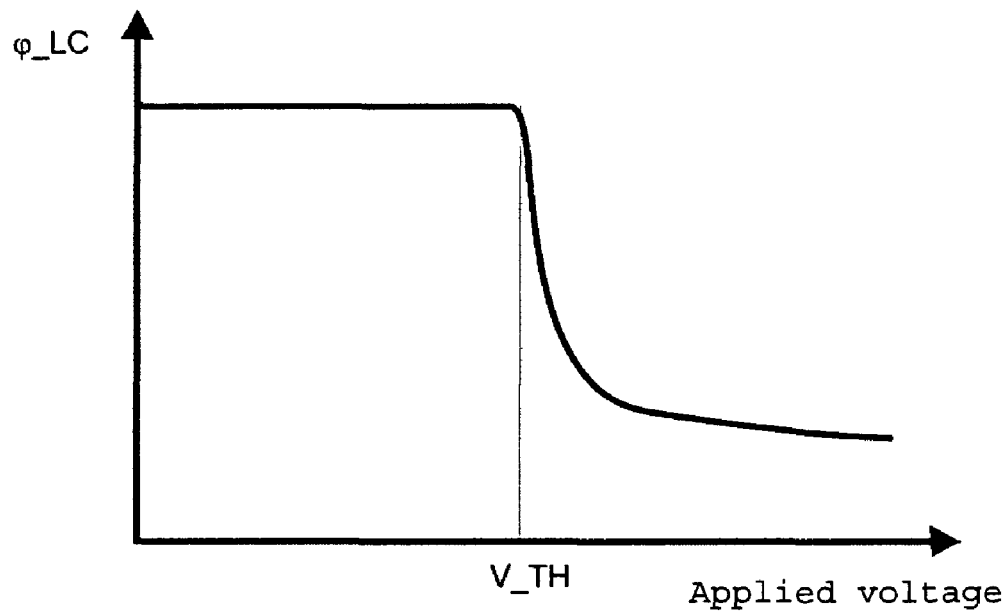
FIG. 4C is a schematic illustration of the behaviour of the total phase difference (de-phasing between the ordinary and extraordinary polarization directions of the radiation with respect to the LC average orientation direction) of the LC layer described in FIG. 4B as a function of the applied voltage. For high enough voltages the phase difference tends to zero.

FIG. 4C is a schematic illustration of the behaviour of the total phase difference (de-phasing between the ordinary and extraordinary polarization directions of radiation with respect to the LC average orientation direction) of the LC layer (80) described in FIG. 4B as a function of the applied voltage. For sufficiently low voltages (V<Vth) and due to the optical anisotropy the total de-phasing of the LC molecules is fixed and defined by the total LC layer (80) thickness and the average orientation of the LC molecules (83). For high enough voltages (V>Vth) the phase difference tends to zero and is defined by relation (4).

Knowing the properties of the LC layer (80) it is then possible to determine with precision the induced de-phasing δ by the relation:

$$\delta = n_o \int_{-d/2}^{d/2} \left[ \frac{n_e}{\sqrt{n_o^2 \sin^2\theta(z) + n_e^2 \cos^2\theta(z)}} - 1 \right] dz \quad (4)$$

in which $n_o$ and $n_e$ are the ordinary and extraordinary refractive indexes of the LC and θ(z) is the average orientation of the LC molecules (83) along the LC layer (80).

In this example, we have considered a SPR sensor (10) with fixed wavelength and a range of incidence angles, and having a LC layer (80) placed in the radiation path between the radiation emitter (20) and the radiation detector (30). The SPR sensor (10) enables the detection of radiation intensities as a function of the incidence angle, the LC layer (80) being built and placed in such a way that it enables the adjustment of the optical phase difference between the TM and TE components of the radiation polarization through optical or electric means.

Figure 5A:
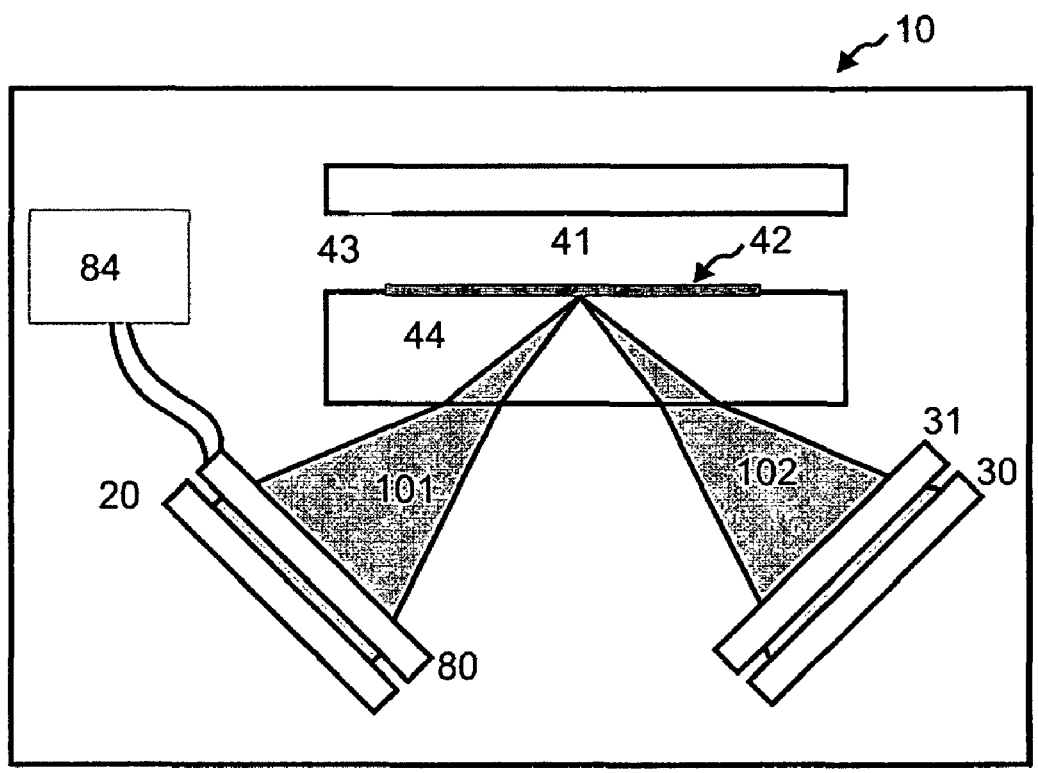
FIG. 5A is a schematic illustration of an SPR detection device in the grating coupling configuration and according to the second example of the present invention, where a LC layer is used to control the de-phasing of the radiation incident on the detection surface.

FIG. 5A is a schematic illustration of an SPR detection device in the grating coupling configuration according to this second embodiment of the present invention. The radiation emitter (20) irradiates a light beam that passes through an LC layer (80) presenting in its rest condition a phase variation between the TM and TE components of the radiation polarization, given by $\delta = \Delta n * D$, in which $\Delta n$ is the birefringence of the LC and D the total thickness of the LC layer (80). The LC layer (80) is connected to an LC controller (84) that enables to control the electric voltages applied to the LC layer (80). The amplitude of the applied electric voltages enables the fine tuning of the phase difference between the TM and TE components of the radiation polarization that is incident on the DS (42). The optical signal from the DS (42) passes through a polarizer (31) and arrives to the radiation detector (30). The analysis of the optical signal in the radiation detector (30) enables the quantitative determination of the analyte concentration in the close proximity of the DS (42).

In this case it is considered favourable that the radiation incident on the DS (42) contains both non-zero polarization components (TM and TE). The TE component does not change in terms of radiation intensity or phase, independently of the incidence angle (besides the classic changes expressed by the Fresnel relations and resulting from the refractive index and extinction coefficients, see reference 7) and depends only on the incident angles and on the refractive indexes of the substrate and the fluid. On the contrary, the TM polarization component changes sharply at a specific incidence angle due to the SPR effect. For example, the phase of the TM polarization component of the radiation shows an abrupt transition, typically over 180° in a range of incidence angles smaller than 10°.

Figure 5B:
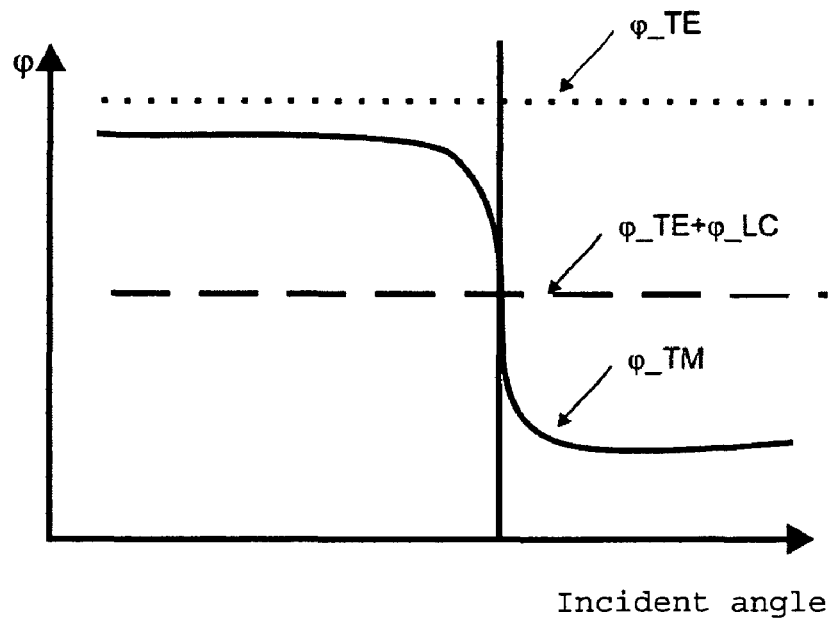
FIG. 5B is a schematic illustration of the evolution of the de-phasing of radiation as a function of the incidence angle on the detection surface for the detection device described in FIG. 5A.

FIG. 5B is a schematic illustration of the evolution of the radiation de-phasing as a function of the incident angle on the DS (42) for the detection surface of the device described in FIG. 5A. The phase $\phi\_TE$ of the TE polarization component from the DS (42) does not show significant changes. The phase $\phi\_TM$ of the TM polarization component changes sharply close to a specific incidence angle in which the SPR effect occurs. Initially the total phase difference between the TE and TM polarization components is typically high. By using an LC layer (80), that induces an additional phase difference $\phi\_LC$ as a function of the applied voltage, it is then possible to properly adjust the phase difference between the two TE and TM polarization components of the radiation incident (101) on the DS (42), in order to have a phase difference of zero at the incidence angle at which the SPR effect occurs.

The detection polarizer (31) is placed in a perpendicular direction to the polarization direction of the incident radiation (102) and between the DS (42) and the radiation detector (30). In this way, when the de-phasing between the two polarization components is zero, one observes a total extinction of light after the detection polarizer and, on the other hand, one observes a maximum of radiation intensity after the detector polarizer (31) for a de-phasing of 90° (quarter-wave). This fact comes from the effect induced by the linear polarizer (31), since the intensity of radiation passing through the polarizer follows the relation (5):

$$I = I_0 \cos^2 \alpha \qquad (5)$$

in which $I_0$ is the intensity of the radiation incident on the polarizer and $\alpha$ is the angle between the linear polarization of the incident radiation (102) and the major direction of the polarizer.

Due to the sharp change on the relative phase of the TM component, one may observe two extinctions of light for two incidence angles corresponding to null or 180° de-phasing. Between these two radiation extinctions there is a local maximum of radiation intensity that corresponds to a de-phasing of 90°, according to FIG. 5C.

Figure 5C:
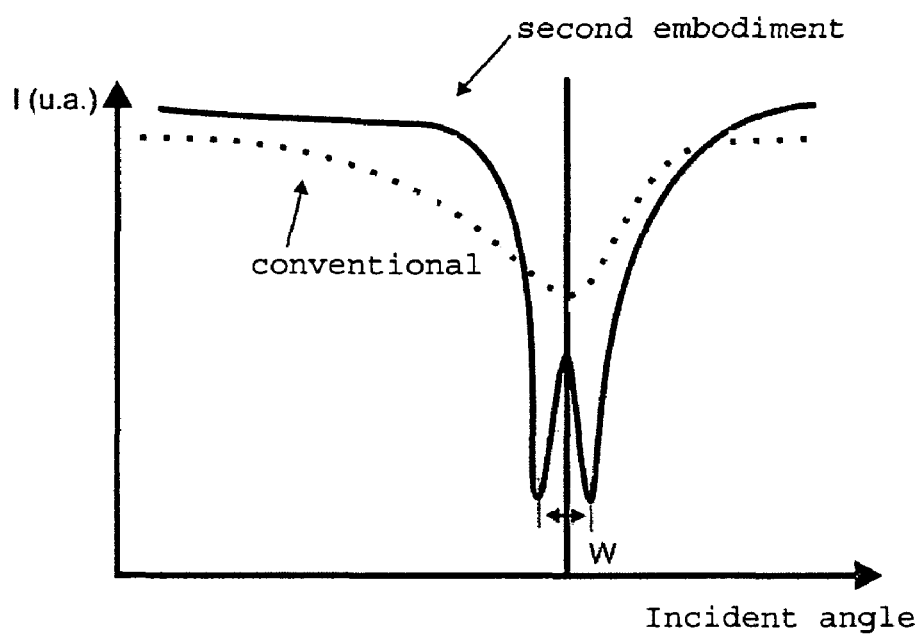
FIG. 5C is a schematic illustration of the SPR signal detected by the radiation detector of a conventional SPR sensor (dashed line) and the sensor for the device described in FIG. 5A (solid line)

FIG. 5C is a schematic illustration of the SPR signal detected by the radiation detector for a conventional SPR detection device (dashed line) and for the device described in FIG. 5A (solid line), in which the detection polarizer (31) is placed approximately parallel to the SPR angle. Due to the sharp change of the TM component relative phase of the radiation coming from the DS (42), after passing through the detection polarizer (31) the signal presents a sharp intensity transition. One observes two minima of radiation intensity spaced by an angular distance W, with a local maximum between them. The angles of minimum intensity correspond to linear polarizations perpendicular to the major direction of the detection polarizer (31). The distance W is found to be minimized when the de-phasing ($\Delta\phi = \phi\_TE + \phi\_LC - \phi\_TM$) is null for the angle of incidence in which the SPR effect occurs.

By applying an electric voltage to the LC layer (80) in order to vary the phase difference between the TM and TE components of the radiation polarization, it is then possible to adjust the angular position of the two light extinctions. The angular distance W between these extinctions increases when moving apart from and decreases when moving closer to the incidence angle at which the SPR effect occurs. Thus, it is possible to control the applied voltage on the LC layer (80) in order to minimize this angular distance W and determine in this way the minimum angular distance that corresponds to the angle at which the SPR effect occurs.

It is then possible, using this invention, to detect simultaneously the phase difference change of the radiation incident and also the angle in which the SPR occurs. The proper control of the total de-phasing induced by the LC layer (80) is feasible since the average orientation of the LC molecules (83) depends on the applied voltage. By combining these two effects (the de-phasing induced by the LC layer and the effect induced by the detection polarizer) it is then possible to obtain a SPR signal with much better contrast when compared with conventional SPR sensors.

The result of the this second embodiment would only be achieved in a conventional SPR sensor using a fixed quarter-wave or another element that would introduce a fixed de-phasing between TM and TE polarization components of the radiation incident on the DS (42), but nevertheless unable to dynamically adjust the de-phasing between both polarization components.

This example may be extended for SPR sensors (10) with different configurations, namely in the prismatic configuration and in the diffraction coupling configuration. It is also possible to obtain the same result when using other means for controlling the LC layer (80) as long as it is possible to properly adjust the average orientation of the LC molecules (83).

It is also possible to use an alternative configuration, in which the polarizer (31) is aligned in perpendicularly to the linear polarization direction for the incidence angle at which the SPR effect occurs. In this case one observes a similar signal to the one presented in FIG. 5C, but with two local maxima spaced by the angular distance W and having a minimum at the incidence angle at which the SPR effect occurs.

One other alternative configuration consists in using a LC layer (80) with a gradient of de-phasing $\phi\_LC$ in a perpendicular direction to the direction of variation of the incident angles. In this case, the optical signal acquired by the radiation detector (30) is two-dimensional, with each line exhibiting the same behaviour described in FIG. 5C.

Figure 5D:
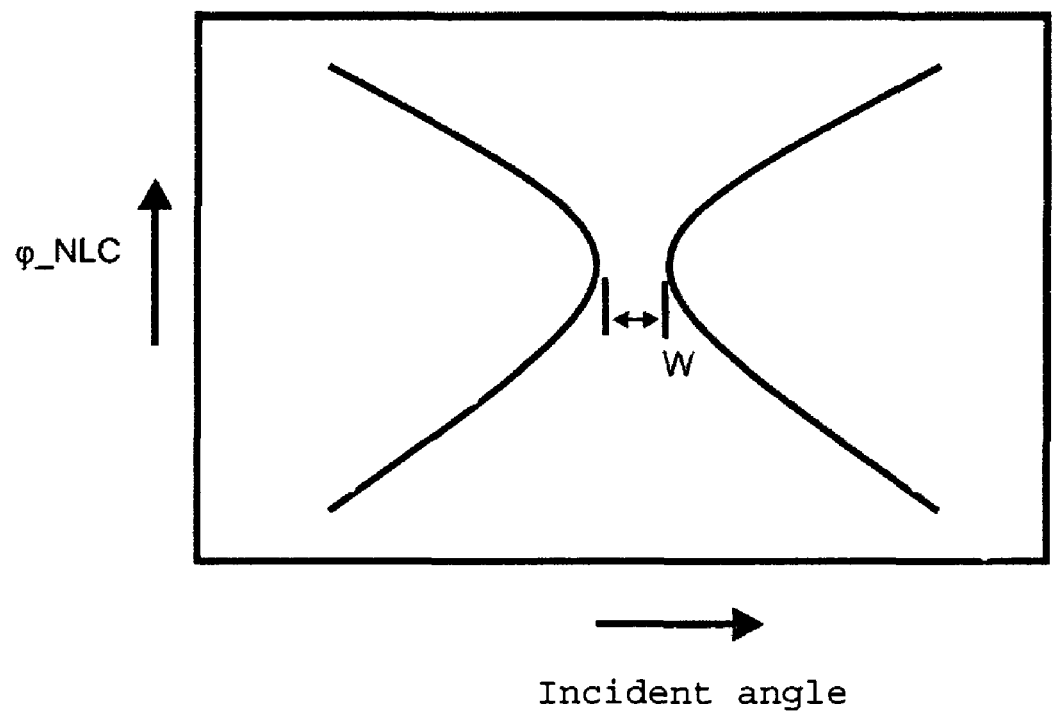
FIG. 5D is a schematic illustration of the evolution of the distance between the two angles at which the minimum of intensity of the SPR optical signal occur (W), as a function of the de-phasing of radiation for the detection device described in FIG. 5A, and in which the LC layer (80) induces a de-phasing perpendicular to the incidence direction.

FIG. 5D is a schematic illustration of the evolution of the angle for the minimum of intensity of the SPR optical signal as a function of the radiation de-phasing for the detection device described in FIG. 5A, and in which the LC layer (80) induces a de-phasing in the perpendicular direction to the variation of the incident angles. In this case, the detection is performed using a two-dimensional radiation detector (30) of matrix type, in which is observed in each line a similar behaviour as described in FIG. 5C. The gradual change of the de-phasing enables the determination in real time of the line corresponding to the minimal distance W between the two local minima of the radiation intensity.

The man of the art may find several advantages when adopting this method, since the proper adjustment of the voltages applied to the LC layer (80) may be applied between signal acquisitions, contrarily to the other configurations previously presented.

All the previous configurations have considered an LC layer (80) placed in between the radiation emitter (20) and the DS (42). This is usually considered preferable due to its simplicity, since it enables the use of a collimated radiation beam and then placing the focusing elements after the LC layer (80).

Figure 6:
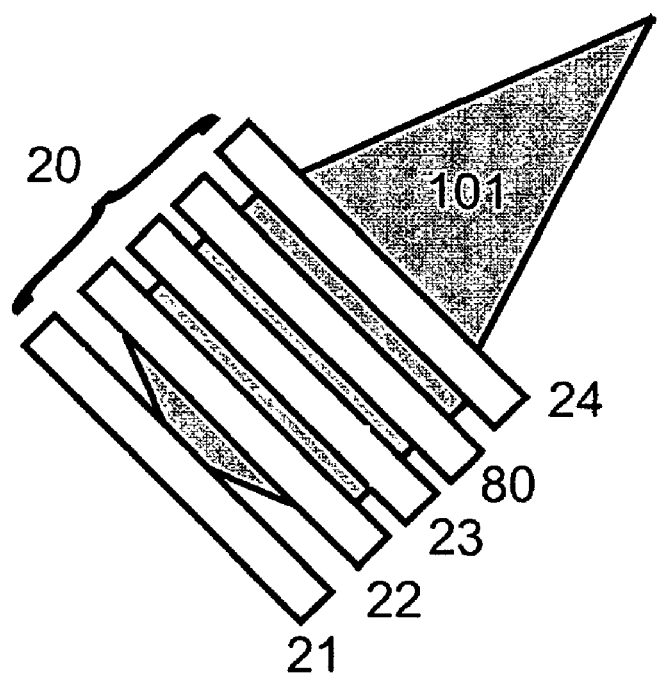
FIG. 6 is a schematic illustration of the optical sub-system of radiation emission for a SPR detection device according to the present invention, in which a collimating lens is positioned after the emitter, followed by a polarizer and an LC layer placed in the collimated radiation path, and finally a focusing lens is used for directing the radiation to the detection surface.

FIG. 6 is a schematic illustration of the optical sub-system of radiation emission for an SPR detection device according to the present invention, in which a collimating lens (22) is used after the radiation emitter (20), and a emitter polarizer (23) placed between the lens and the LC layer (80) in the collimated radiation path. The emitter polarizer (23) is used in order to optimize the linear polarization of the incident radiation beam. After passing through the LC layer (80), the radiation is focused on the DS (42) by means of a focusing lens (24).

The configuration described in FIG. 6 is one of the possible configurations for the emitter sub-system, but other possible combinations might be used in order to obtain the same results previously described. For example, the emitter polarizer (23) might be eliminated when using a laser as the emission element (21), since laser typically emit polarized light. The collimating lens (22) may also be eliminated if the data processing takes into account the effect of the variable incident angle on the polarizer (23) and on the LC layer (80). The elimination of this collimating lens may introduce additional noise, although the man of the art is capable of properly taking into account this last effect on the signal processing algorithms.

It is also possible to consider an alternative configuration in which the LC layer (80) is placed in the optical path between the DS (42) and the radiation detector (30). In this latter case, there will be again the effect of the variable incident angle on LC layer (80) and on the detection polarizer (31) so this effect must be properly considered.

THIRD EXAMPLE

Conventional SPR detection devices typically use a radiation beam incident on the DS (42) in a fixed range of incident angles. This fact may also be a limiting factor in terms of sensitivity and detection range of the SPR detection device. It would then be interesting to use an SPR detection device having the possibility of controlling, in an easy way, the sensitivity limit and/or the detection range by acting on the range of incident angles of the radiation incident on the DS (42).

The third embodiment of the present invention consists of using two LC layers (85) and (86), controlled by an LC controller (84) and placed in between the radiation emitter (20) and the DS (42) in order to properly adjust the incidence angles of the radiation beam incident on the DS (42). A LC layer may behave as a lens due to the effect of local refractive index variation, namely as a function of an external applied voltage (see reference 8).

Figure 7A:
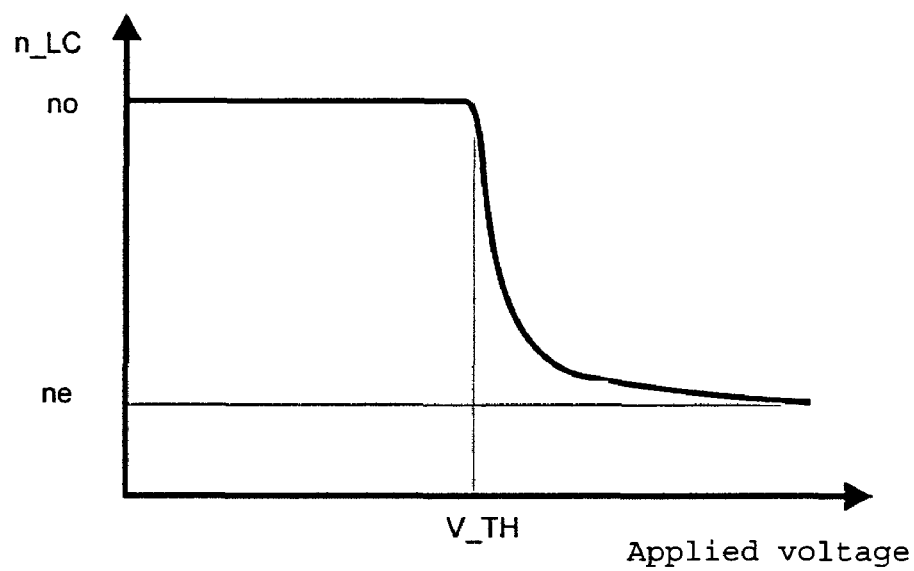
FIG. 7A is a schematic illustration of the resulting refractive index of the LC layer described in FIG. 4B as a function of the applied voltage.

FIG. 7A is a schematic illustration of the resulting refractive index of the LC layer (80) described in FIG. 4B as a function of the applied voltage. The average refractive index of the LC layer (80) changes between the ordinary refractive index $n_o$ for low applied voltages (V<V_TH) and the extraordinary refractive index $n_e$ for sufficiently high applied voltages.

Figure 7B:
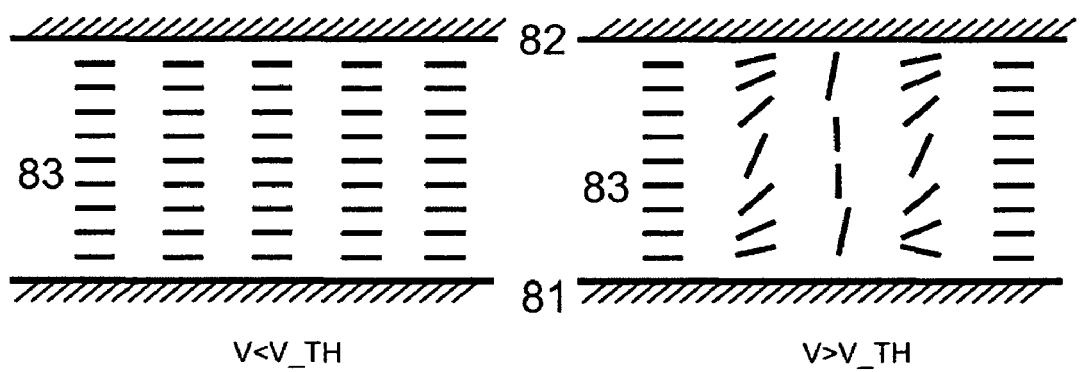
FIG. 7B is a schematic illustration of the average orientation of the molecules inside the LC layers. In the rest condition (V<V_TH) the LC molecules present uniform average orientation (left). Depending on the applied voltage (for V>V_TH), it is possible to create spatial patterns of refractive index.

FIG. 7B is a schematic illustration of an LC layer behaving like an optical lens. In the rest condition (V<V_TH), the average orientation of the LC molecules (83) is uniform and parallel to the top and bottom LC substrates. For sufficiently high electric voltages, the LC molecules tend to be aligned along the electric field and thus present a spatial pattern. It is possible to build an LC Layer (80) that, for a fixed applied voltage, at its center presents a higher alignment of its molecules with respect to the applied electric field when compared to more external regions of the LC layer (80). The gradual change of the average orientation of the LC molecules (83) results in a spatial pattern of the effective refractive index of the LC layer (80) and so this latter behaving like an optical lens.

Figure 7C:
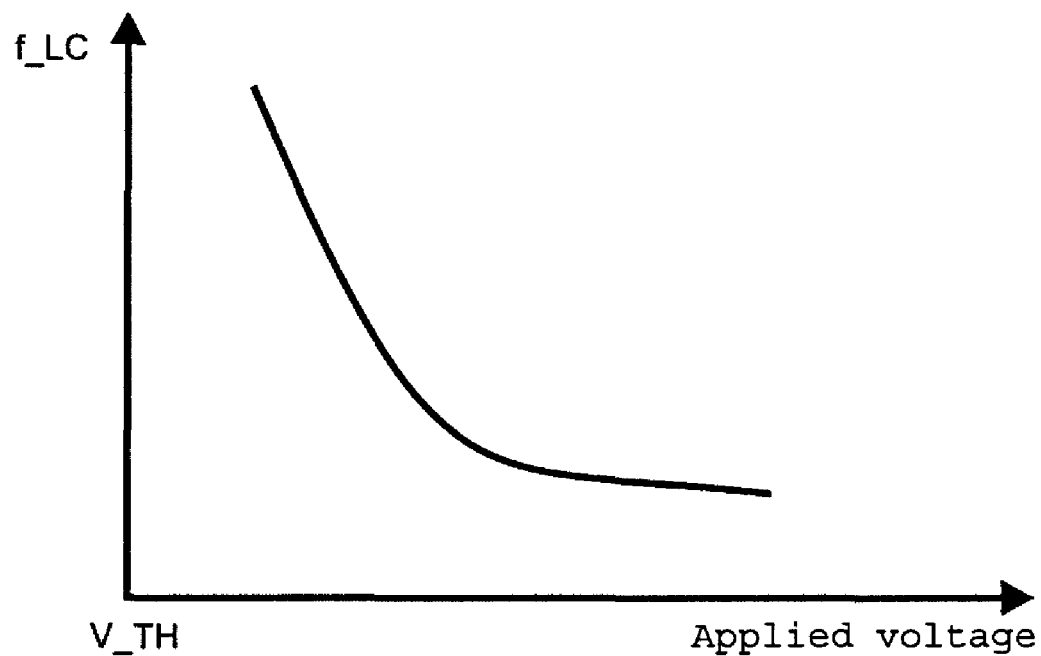
FIG. 7C is a schematic illustration of the equivalent focal distance of the LC layer illustrated in FIG. 7B, as a function of the applied voltage.

FIG. 7C is a schematic illustration of the equivalent focal distance of an LC layer (80) illustrated in FIG. 7B, as a function of the applied voltage. The equivalent focal distance of the LC layer (80) decreases when increasing the applied voltage. Within certain limits, the equivalent focal distance shows a linear dependency with the applied electric voltage.

There are several possible configurations that exploit this effect and enable the use of LC layers as optical lenses (see references 8 and 9). Given the SPR sensor (10) characteristics, it is considered favourable to have a constant and fixed focal length for the radiation incident on the DS (42). The resulting focal length of the association of two thin lenses is given by the relation (6):

$$f = \frac{f_2(d - f_1)}{d - (f_1 + f_2)} \tag{6}$$

in which d is the distance between the two lenses, $f_1$ and $f_2$ are the focal lengths of the lens 1 and lens 2, respectively (see reference 7). The total range of incident angles is defined by $\Delta\alpha$.

Figure 7D:
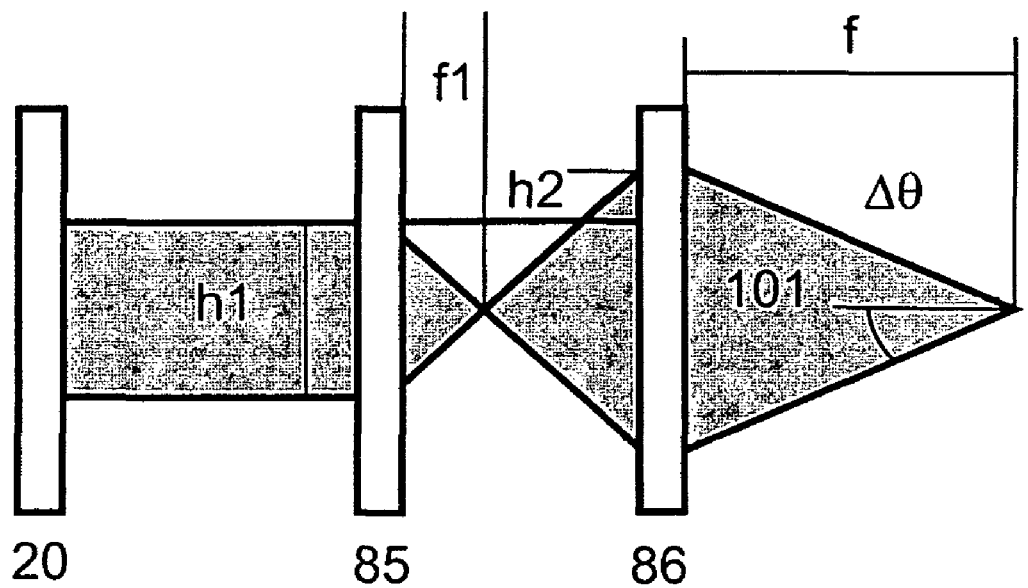
FIG. 7D is a schematic illustration of the optical sub-system of radiation emission for a SPR detection device according to the present invention, in which a group of two LC layers are used to act as focusing lens of variable amplification with constant focal length.

FIG. 7D is a schematic illustration of the optical sub-system of radiation emission for an SPR detection device according to the present invention, characterized in that two LC layers (85) and (86) are used, in order to have it working like a focusing lens of variable amplification with constant focal length. The radiation emitter (20) irradiates a collimated radiation beam onto a first LC layer (85) characterized by an equivalent focal length $f_1$. A second LC layer (86), placed at a distance d from the first LC layer (85) and is characterized by a focal length $f_2$. The group of these two LC layers is built and placed in such a way that it presents a constant focal length f and a controllable range of incident angles $\Delta\theta$, simply by adjusting the electric voltages applied on the LC layers (85) and (86).

The group of LC layers (85) and (86) shows a constant equivalent focal length f and obeys the relation (6). The total range of incident angles Δθ is controllable through the applied electric voltages on the LC layers (85) and (86) and follows the relation (7):

$$\Delta\theta \approx \arctan\left(\frac{h_1}{2} \frac{d^2 - f_1(d + f_2)}{f_2(d - f_1)}\right) \quad (7)$$

This relation (7) is only valid if the LC layers (85) and (86) were much thinner than the distance d. This is the typical case, since common LC layers have a thickness between 1 µm and 100 µm and d is typically between 1 mm and 10 mm. The exact relation for the range of incident angles Δθ and may also be determined when the distance d is of the same order of the LC layer thickness, but in this latter case it becomes difficult to maintain the condition of constant focal length.

The control on the equivalent focal lens of an LC layer may be obtained by applying an external electric voltage, with a typical signal frequency between 1 KHz and 100 KHz, and voltage amplitudes between 0 V and 50 V. The effective refractive index of the LC layer may change with the applied voltage, depending on several parameters, namely: the structure of the LC layer, its thickness, the relation between the elastic, optical and dielectric constants of the LC molecules, the anchoring strength between the LC molecules and the LC substrates, among others. In a simplified approach, and within certain limits, it is possible to observe a linear dependency of the equivalent focal length of an LC layer when varying the applied voltage.

Let us consider, for example, two LC layer (85) and (86), built in such a way that each layer may vary linearly its equivalent focal length between 1 mm and 10 mm, depending on the applied voltage. For example, having 10 V of applied voltages induces an equivalent focal length of 10 mm and 20 V yields 1 mm of focal length). The two LC layers are placed at a distance of 10 mm, and the collimated radiation beam has 5 mm of diameter when arriving to the first LC layer (85). In this example, the radiation incident on the DS (42) will have a total focal length of 20 mm. Now, maintaining this total focal length at 20 mm and according to equations (6) and (7), it is possible to vary the total range of incident angles Δθ from 48° (with V1=20.000 V and V2=14.215 V) to 1.8° (with V1=12.222 V and V2=19.091 V).

The practical use of this example of the present invention may require the man of the art a special care in the measure and control of optical aberrations and distortions induces by the group of LC layers behaving like a variable amplification lens with constant focal length. This determination and control may the obtained with precision (see reference 10) in order to minimize the noise associated to the detection based on the SPR effect.

This third embodiment of the present invention may be extended to other configurations of detection devices based on the SPR effect, namely in the cases of the prismatic configuration or the grating coupling configuration. It may also be considered with advantage other means for controlling the average orientation of the LC molecules (83) of the LC layers (85) and (86), wherein the applied voltage amplitude is kept constant and only the signal frequency is varied. In this case, the man of the art may choose a suitable frequency range wherein the LC molecules (83) response is strongly dependent on the signal frequency.

Another alternative configuration of this embodiment consists in using two LC layers (85) and (86) placed in the optical path between the DS (42) and the radiation detector (30). This last configuration may be considered with advantage since all the elements with high optical quality are placed in the proximity of the radiation emitter (20), and so it may optimize the SPR effect on the DS (42). This latter case may imply the use of an additional detection lens (32), placed in between the DS (42) and the LC layers (85) and (86), in order to have a collimated beam before the first LC layer (85).

Figure 8:
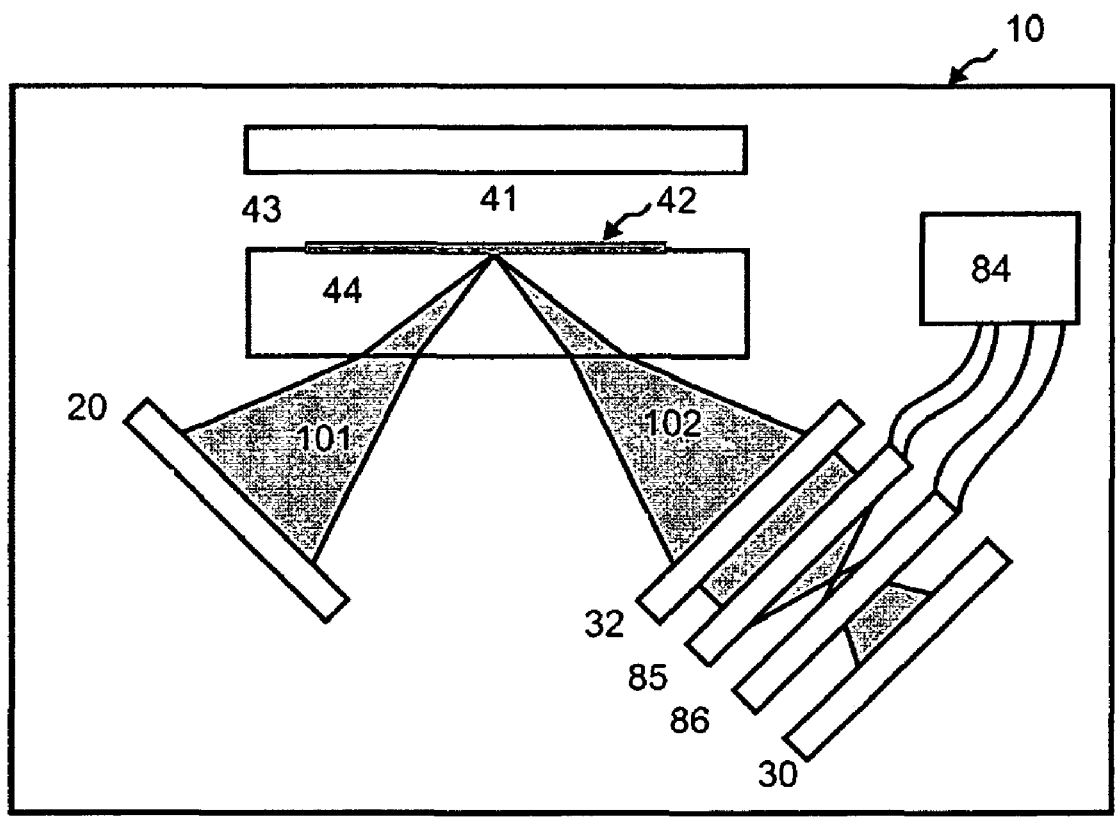
FIG. 8 is a schematic illustration of a detection device according to the present invention, in which a group of two LC layers is placed in between the detection surface and the radiation detector in order to control the radiation signal amplification.

FIG. 8 is a schematic illustration of a detection device according to the present invention, in which a group of two LC layers is placed in between the detection surface (42) and the radiation detector (30) in order to control the radiation signal amplification. The incident radiation (101) is reflected at the DS (42) and the reflected radiation (102) is transmitted through detection lens (32) and then passes through the LC layers (85) and (86) and arrives to the radiation detector (30). The LC layers (85) and (86) are controlled by the LC controlled (84). By properly adjusting the applied voltages on the LC layers (85) and (86) it is possible to control the diverging angle of the reflected radiation (102). This control enables the adjustment of the detection range and sensitivity limit of the SPR sensor (10).

In this case the group of LC layers (85) and (86) enable the control of optical signal amplification around the angle in which the SPR effect occurs. For example, it is possible to defined a minimum acceptable contrast of the SPR optical signal and then gradually adjust the amplification of the group of LC layers (85) and (86) in order to maximize the resolution of the detection device, keeping a signal to noise rate rather constant.

These examples demonstrate some different possible embodiments of the present invention in order to build and use an SPR sensor (10) using LC layers that enables the detection of chemical and/or biological events, with a better performance when compared to conventional SPR detection devices.

| Summary of the abbreviations |
| --- |
| SPR sensor 10 |
|     Radiation emitter 20 |
|         Emission element 21 |
|         Collimating Lens 22 |
|         Emitter Polarizer 23 |
|         Focusing Lens 24 |
|     Radiation Detector 30 |
|         Detection Polarizer 31 |
|         Detection Lens 32 |
|     Fluidic Channels 40 |
|         Detection Zone (DZ) 41 |
|         Detection Surface (DS) 42 |
|         Channels 43 |
|         Substrate 44 |
|     Liquid Crystal (LC) Layer 80 |
|         Bottom LC substrate 81 |
|         Top LC substrate 82 |
|         LC Molecules 83 |
|         LC Controller 84 |
|         First LC Lens Layer 85 |
|         Second LC Lens Layer 86 |
| Prism 90 |
| Incident Radiation 101 |
| Outgoing Radiation 102 |

The invention claimed is:

1. A dynamic detection device based on the Surface Plasmon Resonance effect, comprising:
   (i) a radiation emitter and a radiation detector;
   (ii) a fluidic substrate, placed between the radiation emitter and the radiation detector, containing channels and at least one detection zone, in which a detection surface is built in such a way that it enables the surface plasmon resonance effect to occur;

(iii) a liquid crystal layer, placed in between the radiation emitter and the radiation detector, capable of exhibiting at least two states of orientation, in order to modify at least one of incident radiation on the detector surface and outgoing radiation from the detection surface; and (iv) a controlling means adapted to apply an external voltage with frequencies between 1 KHz and 100 KHz and voltages between 0 Volt and 50 Volts, wherein the control means is further adapted to: change an average orientation of a plurality of liquid crystal molecules of the liquid crystal layer; change an equivalent focal length of the liquid crystal layer; set the liquid crystal layer for one of convergence or divergence of electromagnetic radiation; and dynamically adjust radiation properties of the liquid crystal layer;

wherein the liquid crystal layer is a nematic or twisted nematic liquid crystal layer, and wherein the dynamic detection device enables a determination of chemical and/or biological events through the surface plasmon resonance effect occurring in a close proximity of the detection surface of the detection zone.

2. The dynamic detection device of claim 1, wherein the control means applying an external electrical voltage to the liquid crystal layer produces the following behaviors:

(i) a uniform change in a thickness of the liquid crystal layer;

(ii) a uniform change in an orientation of the liquid crystal molecules in a proximity of borders of the liquid crystal layer; and (iii) a uniform change in an anchoring strength of the liquid crystal molecules in the proximity of the borders of the liquid crystal layer.

* * * * *